United States Patent [19]

Brake

[11] Patent Number: 4,605,788

[45] Date of Patent: Aug. 12, 1986

[54] CATALYTIC PREPARATION OF DIMETHYL ETHER

[75] Inventor: Loren D. Brake, Wilmington, Del.

[73] Assignee: E. I. Du Pont de Nemours and Company, Wilmington, Del.

[21] Appl. No.: 768,936

[22] Filed: Aug. 26, 1985

Related U.S. Application Data

[63] Continuation of Ser. No. 702,842, Feb. 19, 1985, abandoned, which is a continuation of Ser. No. 573,598, Jan. 26, 1984, abandoned, which is a continuation of Ser. No. 394,120, Jul. 1, 1982, abandoned.

[51] Int. Cl.$^4$ .............................................. C07L 41/04
[52] U.S. Cl. .................................................... 568/698
[58] Field of Search .......................................... 568/698

[56] References Cited

U.S. PATENT DOCUMENTS

| | | | |
|---|---|---|---|
| 2,014,408 | 9/1935 | Woodhouse | 260/151 |
| 3,036,134 | 5/1962 | Mattox | 568/698 |
| 3,928,483 | 12/1975 | Chang et al. | 568/698 |
| 4,337,366 | 6/1982 | Fattore et al. | 568/698 |

FOREIGN PATENT DOCUMENTS 403402  1/1938  United Kingdom .

*Primary Examiner*—Howard T. Mars

[57] ABSTRACT

In the preparation of dimethyl ether by the catalytic dehydration of methanol, reaction rate is enhanced and catalyst coking and byproduct formation are significantly reduced when an aluminosilicate containing a high level of alumina is used as the catalyst.

3 Claims, No Drawings

CATALYTIC PREPARATION OF DIMETHYL ETHER

This application is a continuation of application Ser. No. 702,842, filed Feb. 19, 1985, which is a continuation of Ser. No. 573,598, filed Jan. 26, 1984, which is a continuation of Ser. No. 394,120, filed July 1, 1982, all of which are abandoned.

DESCRIPTION

Technical Field

This invention relates to an improved method for the preparation of dimethyl ether by the catalytic dehydration of methanol. It is more particularly directed to such a method in which the catalyst used is an aluminosilicate containing a high proportion of alumina.

BACKGROUND AND SUMMARY OF THE INVENTION

Dimethyl ether is a commodity in the chemical industry, widely used as a starting material in the preparation of other chemicals, e.g., dimethyl sulfate, and more recently, as a propellant in aerosol containers.

One of the commonly used methods for preparing dimethyl ether is the catalytic dehydration of methanol, using a phosphoric acid-alumina catalyst.

While that process is generally satisfactory, the catalyst has a tendency to coke, which makes it necessary to replace it more frequently than is desirable. By "coke" is meant the phenomenon by which the surface of the catalyst becomes coated with carbon, thus blocking its pores and reducing its effectiveness.

It has now been found that this coking can be minimized if, instead of the phosphoric acid-alumina catalyst, one uses an aluminosilicate catalyst containing 1–20% silica and 80–99% alumina. Surprisingly, use of such a catalyst according to the invention not only reduces the amount of coking but also significantly increases the rate of the dehydration reaction over that obtained with the phosphoric acid-alumina catalyst, and greatly reduces the number and amounts of byproducts formed, notably hydrogen, carbon monoxide, methane, ethane, propane, ethylene, propylene and various ethers having high boiling points.

DETAILED DESCRIPTION OF THE INVENTION

The catalytic dehydration of methanol to form dimethyl ether is well known and is described in detail in U.S. Pat. No. 2,014,408 to John C. Woodhouse.

The reaction proceeds according to the general equation

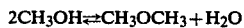

$$2CH_3OH \rightleftharpoons CH_3OCH_3 + H_2O$$

The product of the reaction is principally a mixture of dimethyl ether, unreacted methanol and water.

The reaction is ordinarily conducted continuously in a column reactor, in the vapor phase, generally at a maximum reactor bed temperature of 200°–500° C., preferably 275°–420° C., and a pressure ranging from ambient to 3447 kPa (gauge), preferably 1034–1723 kPa (gauge). The catalyst is packed into the reactor in the customary way, and the vaporized and preheated (200°–300° C.) methanol is passed through it, preferably downwardly. Residence time of the methanol in the reactor is determined according to well-known chemical engineering principles, as are the methods of recovering the dimethyl ether from the reactor effluent and the methods of refining it.

The catalysts used according to the invention are aluminosilicates containing 1–20% by weight of silica and 80–99% by weight of alumina, preferably 1–10% of silica and 90–99% of alumina, even more preferably about 6% of silica and about 94% of alumina. A catalyst especially suited for use according to the invention is an aluminosilicate containing about 6% silica and about 94% alumina, sold by Harshaw Chemical Company of Beachwood, Ohio, as Al-1602.

The catalysts can be made by the well-known method of coprecipitating appropriate amounts of sodium silicate and sodium aluminate from aqueous solution by bringing the solution to a pH of about 8 with hydrochloric acid, at a temperature of 50°–70° C. The resulting gel, a mixture of hydroxides, is recovered, washed free of chlorides, dried to a free-flowing powder, pelleted and then calcined at 450°–650° C. to give a material which can be used directly as the catalyst.

The catalyst is customarily used in the form of cylindrical pellets. Pellet size is selected according to recognized chemical engineering principles, and is usually in the range 2–130 mm in all dimensions. The pore volume, pore size and total surface area of the pellets are likewise a matter of choice, and will generally be in the ranges of 0.2–0.8 cc/g, greater than 25 angstrom units, and 100–250 m$^2$/g, respectively.

EXAMPLE

Best Mode

In the following description, all parts are by weight.

Six hundred parts of Harshaw Al-1602 in the form of 6.5 mm cylindrical pellets were packed into an adiabatic column reactor having a length/diameter ratio of 5.

Methanol, preheated to 270° C., was then continuously fed into the top of the reactor. The vapors were passed downwardly through the catalyst bed at a rate of 9000 parts per hour. Pressure in the reactor was 1034 kPa (gauge) and the reactor bed temperature reached a maximum of 390° C.

The vapors leaving the reactor were condensed to give a product having the average composition
Dimethyl ether: 57% by weight
Methanol: 20% by weight
Water: 23% by weight.

I claim:

1. In the preparation of dimethyl ether by the catalytic dehydration of methanol, the improvement which comprises using as the catalyst an aluminosilicate which consists of, by weight 1–20% of silica and 80–99% alumina, said aluminosilicate being a calcined coprecipitation product.

2. The process of claim 1 in which the catalyst consists of 1–10% of silica and 90–99% of alumina.

3. The process of claim 1 in which the catalyst consists of about 6% of silica and about 94% of alumina.

* * * * *